(12) United States Patent
Lindeman et al.

(10) Patent No.: US 8,618,370 B2
(45) Date of Patent: Dec. 31, 2013

(54) METHOD FOR TRANSFERRING ONE OR MORE GENETIC TRAITS FROM A PLANT OF THE PURPLE-FLOWERED CAPSICUM SPECIES TO A PLANT OF THE WHITE-FLOWERED CAPSICUM SPECIES

(75) Inventors: Wouter Lindeman, Enkhuizen (NL); Iris Alke Heidmann, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 13/232,466

(22) Filed: Sep. 14, 2011

(65) Prior Publication Data
US 2012/0066797 A1 Mar. 15, 2012

Related U.S. Application Data

(62) Division of application No. 11/992,503, filed as application No. PCT/EP2005/054759 on Sep. 22, 2005, now Pat. No. 8,022,278.

(51) Int. Cl.
*A01H 5/00* (2006.01)
*A01H 1/04* (2006.01)

(52) U.S. Cl.
USPC .......................... 800/317.1; 800/265; 800/269

(58) Field of Classification Search
None
See application file for complete search history.

(56) References Cited

PUBLICATIONS

Molchova et al. Capsicum Newsletter 1: 39-41 (1982).*
Onus et al. Turkish Journal of Botany 24: 319-328 (2000).*
Nikova et al. In Vitro Cellular and Developmental Biology, Animal, vol. 37, No. 3, Part 2, p. 40A (2001).*
Zijlstra et al. HortScience 26(5): 585-586 (1991).*
Sahin et al. Plant Disease 82(7): 794-799 (1998).*
Quiros, C. Caspcium spp online fact sheet from www.plantsciences.ucdavis.edu/vc221/pepper (2003).*

* cited by examiner

*Primary Examiner* — David T Fox
(74) *Attorney, Agent, or Firm* — Morrison & Foerster LLP

(57) ABSTRACT

The present invention relates to a method for transferring one or more genetic traits from a purple-flowered *Capsicum* species plant comprising said genetic trait, to a white-flowered *Capsicum* species plant, said method comprising the steps of: (a) preparing a first hybrid plant comprising said genetic trait by crossing a first purple-flowered *Capsicum* species comprising said genetic traits with a second purple-flowered *Capsicum* species; (b) preparing a second hybrid plant by crossing said first hybrid plant with a first white-flowered *Capsicum* species plant; (c) crossing said second hybrid plant with said first purple-flowered *Capsicum* species plant to produce first progeny plants; and (d) preparing a third hybrid plant by crossing the first progeny plants obtained in step (c) with a second white-flowered *Capsicum* species plant to produce second progeny plants, and selecting the third hybrid plant from the second progeny plants comprising said one or more genetic traits.

4 Claims, 6 Drawing Sheets

C. eximium

FIG. 2A

C. pubescens plants with desired resistance

FIG. 2B

C. frutescens

Product of step I

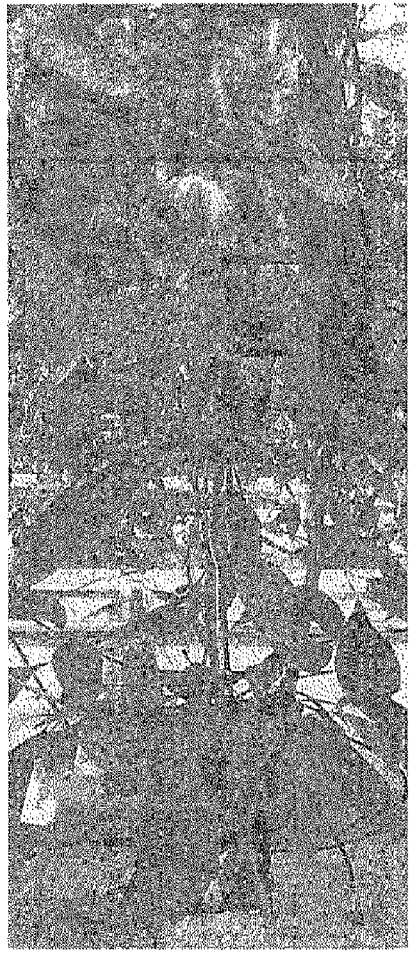
C. annuum
C. chinense
FIG. 4B    FIG. 4C
Product of C.pub, C. exi and C. frut.
FIG. 4A Product of self pollinated C.pub, C. ex, C. frut plant combined with C. chin and C. ann. hybrid

  
FIG. 6A　　　　FIG. 6B　　　　FIG. 6C
FIG. 6D

METHOD FOR TRANSFERRING ONE OR MORE GENETIC TRAITS FROM A PLANT OF THE PURPLE-FLOWERED CAPSICUM SPECIES TO A PLANT OF THE WHITE-FLOWERED CAPSICUM SPECIES

CROSS-REFERENCE

This application is a divisional of U.S. Utility Application Ser. No. 11/992,503, now U.S. Pat. No. 8,022,278, which was filed on May 19, 2008, which is a national stage application filed under 35 U.S.C. 371 of International Application No. PCT/EP2005/054759 filed on Sep. 22, 2005, each of which are incorporated herein by reference.

FIELD OF THE INVENTION

The present invention relates to a method for transferring one or more genetic traits from a plant of the purple-flowered *Capsicum* species comprising-said genetic trait, to a plant of the white-flowered *Capsicum* species. The invention further relates to the plants per se, as well as to the fruits, seeds and other plant parts derived from said plants.

BACKGROUND OF THE INVENTION

The genus *Capsicum* belongs to the large family of the Solanaceae. Several species of the *Capsicum* group are valuable crops that are grown in open fields or under protected conditions in many countries all over the world. *Capsicum* species with pungent fruits are generally used as a spice, either fresh, dry or extracted. Species with nonpungent fruits in a big variety of shapes and colours, commonly known as sweet peppers, are widely used as vegetable.

The genus *Capsicum* can be divided in two distinct groups based on the flower colour: the white-flowered group, comprising e.g. the closely related species *C. annuum, C. frutescens, C. baccatum, C. chacoense, C. galapagoense, C. practermissum* and *C. chinense*, and the purple-flowered group, comprising e.g. *C. tovarii, C. pubescens, C. eximium* and *C. cardenasii*. Of the white-flowered group *Capsicum annuum,* and its closely related species *C. frutescens* are the best known domesticated species, which are mainly used for the production of sweet and hot peppers for processing and consumption.

*Capsicum,* like other plants, is attacked by many pests and diseases, including insects, nematodes, fungi, bacteria and viruses. One of such bacterial diseases is bacterial leafspot, caused by the bacterium *Xanthomonas campestris* pv. *vesicatoria*. Bacterial leafspot of *Capsicum* can be recognized by numerous angular spot on the leaves. Initially, the spots are water-soaked. Leaves infected at an early stage become deformed. Often the margins of affected leaves are rimmed with a narrow band of necrotic tissue. Infected *Capsicum* leaves drop prematurely, by which the fruit is exposed to sun which may result in sun scald, secondary fruit rots and reduced yields. *Capsicum* fruits rarely show symptoms but may drop if infected early.

*X. vesicatoria* is widespread and damaging to *Capsicum* in particular in field-grown crops in warm-temperate and tropical countries, and thus has a large economic impact. Control of the disease relies principally on the production of plants from healthy (treated) seeds and on preventive steps taken during the entire season.

Useful resistances to such diseases, as well as other traits such as fruit quality characteristics etc., may exist in wild or other domesticated species of *Capsicum,* such as for example in *C. pubescens* which carries unique and specific traits, such as the resistance against certain races of the bacterium *Xanthomonas vesicatoria,* that are not present in the white flowering species. It thus may be advantageous to transfer such favourable genetic traits, such as any resistance gene, from the distinctly related purple-flowered *C. pubescens* to the commonly used white-flowered species such as *C. annuum* and/or *C. frutescens*.

It is well known, however, that strong crossing barriers of varying degree exist between the different species of the *Capsicum* genus. Some crosses have even been proven impossible, and other crosses are only possible with the help of in vitro culture techniques, such as embryo rescue. In addition, in most cases the products derived from said crosses are completely or partially sterile which makes them not accessible for any further breeding purposes.

A need therefore exists for a method by which desirable genetic traits can be transferred between the different purple and white flowered *Capsicum* species.

SUMMARY OF THE INVENTION

The object of the present invention is to provide a method for transferring one or more genetic traits, such as, but not limited to, resistance genes, from plants of the purple-flowered *Capsicum* species to plants of the white-flowered *Capsicum* species.

This is achieved by providing a method, comprising the steps of:
(a) preparing a first hybrid plant comprising said genetic trait by crossing a first plant of the purple-flowered *Capsicum* species comprising said genetic trait with a second plant of another purple-flowered *Capsicum* species, and selecting from the progeny thereof plants comprising said genetic trait;
(b) preparing a second hybrid plant by crossing said first hybrid plant comprising said genetic trait, with a first plant of the white-flowered *Capsicum* species;
(c) crossing said second hybrid plant with said first plant of the purple-flowered *Capsicum* species comprising said genetic trait, and selecting from the progeny thereof plants comprising the genetic trait;
(d) preparing a third hybrid plant by crossing the plants obtained step c) with a second plant of the white-flowered *Capsicum* species, and selecting from the progeny thereof plants comprising the genetic trait;

According to the present invention, for the first time a genetic trait has been successfully transferred from a purple-flowered *Capsicum* species to a white-flowered *Capsicum* species. The method of the present invention is based on a suitable combination of several interspecific crosses, as well as crosses that serve as a kind of bridge to the next species (FIG. 1). The desired genetic traits can for example be followed by molecular markers or bio-assay according to well-known molecular biological techniques known to the skilled person.

According to a preferred embodiment of the present invention, the method further comprises:
(e) selecting plants obtained in step (d) not comprising the genetic trait and crossing these plants with said first plant of the purple-flowered *Capsicum* species comprising said genetic trait, and selecting from the progeny thereof plants comprising the genetic trait; and
(f) preparing a fourth hybrid plant by crossing the plants obtained step (e) with a second plant of the white-flowered *Capsicum* species, and selecting from the progeny thereof plants comprising the genetic trait. In this way, plants that are obtained in step (d) of the method of the invention that do not comprise the genetic trait, still can be used further in the method of the invention.

According to a further preferred embodiment, the method further comprises:

(g) preparing a fifth hybrid plant by crossing the fourth hybrid plant comprising the genetic trait with a second plant of the white-flowered *Capsicum* species, and selecting from the progeny thereof plants comprising the genetic trait. Thus, a stable white-flowered plant is obtained comprising the genetic trait of interest derived from the purple-flowered species but with all the quality aspects of the white-flowered species.

Preferably, after step (b) the second hybrid plant is self-pollinated and the progeny thereof is used in step (c) in order to fix the resistance, to improve fertility aspects and to obtain homozygous, genetically stable plants carrying the desired trait(s).

According to another preferred embodiment, the plants obtained in step (c) are self-pollinated and the progeny thereof is used in step (d), again in order to fix the resistance, to improve fertility aspects and to obtain homozygous, genetically stable plants carrying the desired trait(s).

In addition, according to other preferred embodiments, the plants obtained in step (d) are self-pollinated and the progeny thereof is used in step (e), and/or the plants obtained in step (e) are self-pollinated and the progeny thereof is used in step (f).

According to the present invention embryo rescue techniques are applied whenever it is beneficial to the process in terms of obtaining hybrid plants or speeding up the process.

Preferably, the first plant of the purple-flowered *Capsicum* species is selected from the group consisting of *C. pubescens, C. eximium*, and *C. cardenasii*, more preferably the first plant of the purple-flowered *Capsicum* species is *C. pubescens*. The greatest genetic distance in the genus *Capsicum* is between the species *C. pubescens* and *C. annuum/frutescens*. Direct crosses between these species have been proven impossible until now, even with the help of embryo rescue. By using the method of the present invention, however, a totally new gene pool becomes accessible to the species of *C. annuum* and/or *C. frutescens*.

According to the invention, the second plant of the purple-flowered *Capsicum* species is selected from the group consisting of *C. pubescens, C. eximium*, and *C. cardenasii*, preferably the second plant of the purple-flowered *Capsicum* species is *C. eximium* or *C. cardenasii*, preferably *C. eximium*. Preferably, the first plant is selected from another species than the second plant of the purple-flowered *Capsicum* species.

In a preferred embodiment of the invention, the first plant of the white-flowered *Capsicum* species is selected from the group consisting of *C. baccatum, C. frutescens, C. chinense, C. annuum*, and hybrids thereof. Preferably, the first plant of the white-flowered *Capsicum* species is *C. frutescens*.

The second plant of the white-flowered *Capsicum* species is preferably selected from the group consisting of *C. baccatum, C. frutescens, C. chinense* and *C. annuum*, and hybrids thereof, more preferably the second plant of the white-flowered *Capsicum* species is *C. chinense, C. annuum* and/or a hybrid thereof.

According to the present invention a hybrid is a plant obtained from a cross between two different species of the *Capsicum* genus, e.g. a cross between a plant of the species *C. chinense* and a plant of the species *C. annuum* (interspecific cross), or a plant obtained from a cross between populations or cultivars of a single species (intraspecific cross).

According to a further preferred embodiment of the invention, the genetic trait is a resistance gene against a specific *Capsicum* disease attacking all cultivated species of *Capsicum*. By transferring one or more resistance genes from distinctly related species of the *Capsicum* genus to commonly used species not naturally having such resistance genes, new resistant plants are provided. As a consequence, the use of environmental undesirable chemical treatments may for example be reduced or even abandoned. However, also other genetic traits, such as other resistance genes, fruit quality characteristics such as shape, taste and colour, improved yield, fruit set, and resistance against abiotic stress (e.g. cold/salt) may be transferred using the method of the present invention.

In a particular preferred embodiment, the resistance gene is the Bs4 gene, conveying resistance to the bacterial disease *Xanthomanas campestris* pv. *vesicatoria* race I, II, IV and VI.

The present invention further relates to plants, obtainable by the method as described above.

In particular, the invention relates to plants of the white-flowered *Capsicum* species, comprising a genetic trait derived from a plant of the purple-flowered *Capsicum* species said plants comprising a genetic trait which normally is not present in the white-flowered species.

In a preferred embodiment, the plant is selected from the group consisting of *C. baccatum, C. frutescens, C. chinense, C. annuum*, and hybrids thereof, preferably, the plant is *C. chinense, C. annuum* and/or hybrids thereof.

According to a preferred embodiment of the invention, the genetic trait is a resistance gene against a *Capsicum* disease, in particular the resistance gene is the Bs4 gene, conveying resistance to the bacterial disease *Xanthomanas campestris* pv. *vesicatoria* race I, II, IV and VI.

Furthermore, the present invention relates to fruits, seeds and other plant parts derived from the plants described above, wherein the other plant parts may be selected from the group consisting of seeds, cuttings, runners, and meristem.

BRIEF DESCRIPTION OF THE DRAWINGS

The present invention is illustrated by the following Example and Figures, which are not intended to limit the scope of the invention in any way.

FIGS. 2A-2B are photographs of a *C. eximium* plant (A) and a *C. pubescens* PI235047 (B) plant with the desired resistance gene used in a first step of a preferred embodiment of the method of the invention;

FIGS. 4A-4C show examples of a second hybrid plant (A), and photographs of *C. annuum* (B) and *C. chinense* (C);

FIGS. 6A-6D show *C. annuum* plants carrying the resistance genes derived from *C. pubescens*.

DETAILED DESCRIPTION OF THE INVENTION

EXAMPLE

Figure 1:
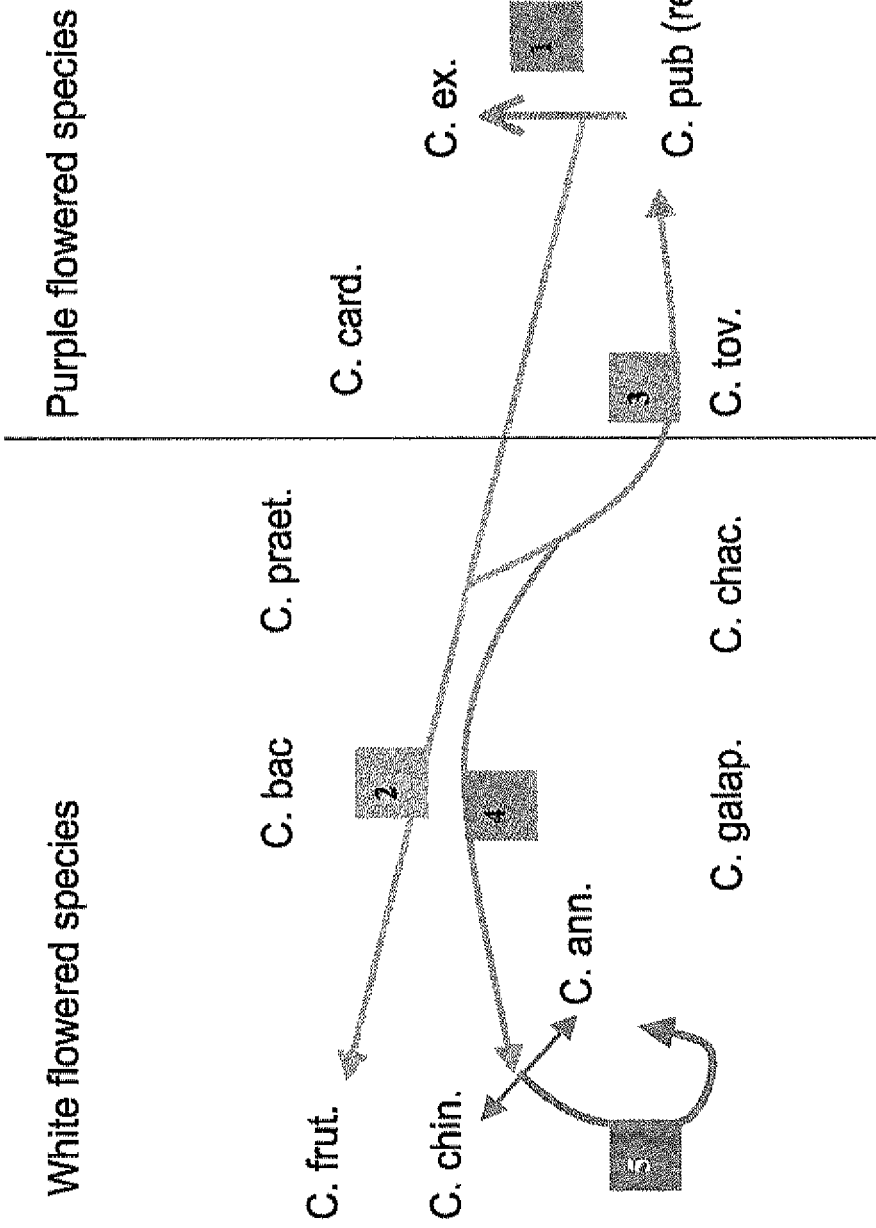
FIG. 1 schematically shows the steps of the method of the present invention.
Figure 3B:
FIG. 3B is a photograph of *C. frutescens*_P1238059.
Figure 3A:
FIG. 3A shows an example of a first hybrid plant, i.e. the product obtained in the first step of the method of the invention.
Figure 5:
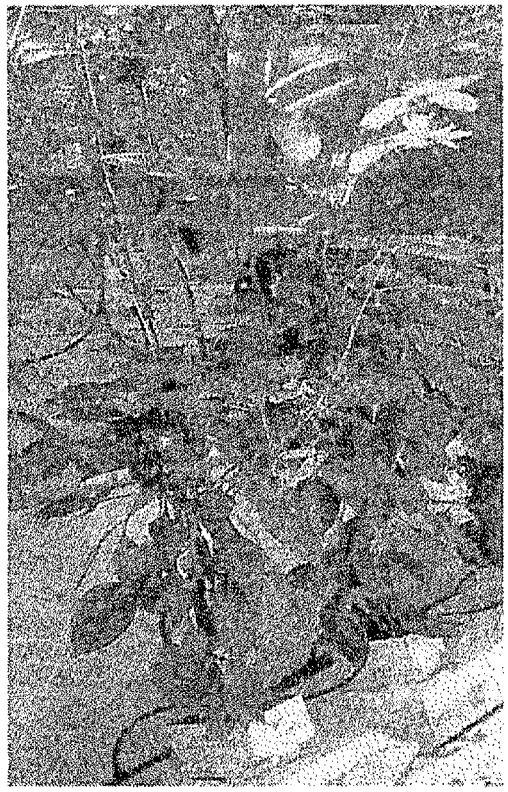
FIG. 5 is a photograph of the product of the self-pollinated (((*C. pubescens*×*C. eximium*)×*C. frutescens*)×(*C. chinense*× *C. annuum*)

Methods:

Seeds were sown on vermiculate, potted into rockwool, blocks, and fertilized and propagated until flowering. Flowerbuds were emasculated and pollinated with the chosen fatherlines. Between 24-28 days after pollination fruits were harvested, surface sterilised and opened under sterile conditions. Embryos from all seeds were isolated aseptically and transferred to embryo rescue (ER) medium as described by Sibi et al., (Aim. Amelior. Plantes, 29: 583-606, 1979). After 1-2 weeks well developed plants were transferred to MS medium (Murashige T. and Skoog F., Physiol. Plant 15: 473497, 1962), supplemented with 0.8% agar and 20 g/l sucrose. Plants with a well developed root system were subsequently transferred to the greenhouse and adapted carefully to its conditions.

Leaves of 4-6 weeks old plants were detached and inoculated with *Xanthomonas campestris vesicatoria* race VI to select the resistant plants. The bacterial clone is stored in the freezer and grown on agar medium one week before inoculation at 22° C. The suspension for inoculation is prepared by resuspending the bacteria in demineralised water. The bacteria suspension was applied to the leaves with a syringe. Inoculated leaves are kept in boxes covered with glass in a climate room at 22° C. for two days. Leaves of resistant plants show a light brown and dry spot at the site of inoculation caused by a hypersensitivity reaction (HR). Leaves of susceptible plants show no reaction or a water soaked lesion at the site of inoculation depending on the time of incubation. Absence of a hypersensitivity reaction thus is indicative of the absence of the Bs4 gene. Resistant control is *C. pubescens* P1235047, susceptible control is a susceptible *C. pubescens* accession.

Crosses:

A first hybrid plant was prepared by crossing *Capsicum pubescens* P1235047 (male, FIG. 2B) (United states Department of Agriculture), comprising the Bs4 resistance gene, with *Capsicum eximium* (female, FIG. 2A). 37 hybrid plants (FIG. 3A), comprising the resistance gene, were obtained.

A second hybrid plant was subsequently prepared by crossing *C. frutescens* PI 238059 (male, FIG. 3B) with the first hybrid plants comprising the resistance gene (female). None of the second hyrid plants plants derived from this cross expressed the resistance.

Subsequently, the second hybrid plant (female, FIG. 4A) was crossed with *Capsicum pubescens* P1235047 (male). Two resistant plants were obtained. These plants were fertile and accordingly F2 seeds were obtained.

In addition, hybrids of *C. annuum* (FIG. 4B) and *C. chinense* (FIG. 4C) were made by crossing individuals of *C. chinense* PBC306 (Asian Vegetable Research and Development Center) with individuals of a *C. annuum* plant. The product of this cross was again crossed with *C. annuum*. Subsequently F2 seeds were obtained.

Subsequently, a third hybrid plant (FIG. 5) was prepared by crossing the resistant plants derived from the cross of the second hybrid plant with *C. pubescens* or plants derived from the F2 seeds thereof, with plants derived from the F2 seeds of the *C. annuum/C. chinense* hybrid. The resistant products from this cross were further crossed with pure *C. annuum* lines.

In addition, plants derived from said cross that were susceptible for Xcv6, were crossed again with *C. pubescens* PI235047. The resistant plants derived from that cross were then selfed and F2 seeds were obtained. Resistant plants derived from that cross were subsequently again crossed with a line derived from the hybrid *Abdera* AMA12. This hybrid is a cross between *C. chinense* and *C. annuum*. The resistant plants resulting from said last cross were selfed and F2 seeds were obtained. In addition, the plants derived from the selfing of the last mentioned cross with P1235047 were further crossed with several *C. annuum* parental lines.

As a result, *C. annuum* plants were obtained carrying the Bs4 resistance gene derived from *C. pubescens* (FIG. 6). These result clearly shows that it is possible to introduce traits from the purple-flowered *Capsicum* species into the white-flowered *Capsicum* species, using the method of the present invention.

The invention claimed is:

1. A fertile white-flowered *Capsicum* species plant, comprising one or more genes derived from a purple-flowered *Capsicum* species plant; wherein the white-flowered *Capsicum* species plant is *Capsicum chinense, Capsicum annuum*, or a hybrid there between; wherein the one or more genes comprises a resistance gene against a *Capsicum* disease; and wherein the resistance gene is the bacterial spot disease resistance protein 4 (Bs4) gene, conveying resistance to bacterial *Xanthomonas campestris pv. vesicatoria* race I, III and IV disease.

2. The fertile white-flowered *Capsicum* species plant of claim 1 wherein the white-flowered *Capsicum* species plant is *Capsicum chinense*.

3. The fertile white-flowered *Capsicum* species plant of claim 1 wherein the white-flowered *Capsicum* species plant is *Capsicum annuum*.

4. The fertile white-flowered *Capsicum* species plant of claim 1 wherein the white-flowered *Capsicum* species plant is a hybrid between *Capsicum chinense* and *Capsicum annuum*.

* * * * *